United States Patent [19]

Holick et al.

[11] Patent Number: 4,661,294

[45] Date of Patent: Apr. 28, 1987

[54] BIOLOGICALLY ACTIVE 1-THIO DERIVATIVES OF VITAMIN D

[75] Inventors: Michael F. Holick, Sudbury; Brian de Costa, Cambridge, both of Mass.

[73] Assignee: The General Hospital Corporation, Boston, Mass.

[21] Appl. No.: 712,712

[22] Filed: Mar. 18, 1985

[51] Int. Cl.$^4$ .......................... C07J 9/00; A61K 31/59
[52] U.S. Cl. ................................................ 260/397.2
[58] Field of Search ...................... 514/167; 260/397.2

[56] References Cited

U.S. PATENT DOCUMENTS

| | | | |
|---|---|---|---|
| 3,158,626 | 11/1964 | Stuckwisch et al. | 260/397.2 |
| 3,627,757 | 12/1971 | Komeno | 260/397.2 |
| 3,715,350 | 2/1973 | Hamashima | 260/397.2 |
| 4,188,345 | 2/1980 | De Luca et al. | 568/665 |
| 4,225,596 | 9/1980 | De Luca et al. | 514/167 |
| 4,234,493 | 11/1980 | De Luca et al. | 549/396 |
| 4,269,777 | 5/1981 | De Luca et al. | 260/397.1 |
| 4,367,177 | 1/1983 | De Luca et al. | 260/397.2 |
| 4,410,515 | 10/1983 | Holick et al. | 423/648 R |
| 4,448,726 | 5/1984 | De Luca et al. | 260/397.2 |
| 4,521,410 | 6/1985 | Holick et al. | 260/397.2 |
| 4,560,557 | 12/1985 | Wilson et al. | 260/397.2 |

OTHER PUBLICATIONS

Holick et al., Biochemistry, vol. 10, No. 14, pp. 2799–2804 (1971).
Sheves et al., J. Am. Chem. Soc., vol. 97, pp. 6249–6250 (1975).
Haussler et al., Life Sci., vol. 18, pp. 1049–1056 (1976).
Paaren et al., Arch. Biochem. Biophys., vol. 209, No. 2, pp. 579–583 (1981).
Sheves et al., Tetrahedron Letters, No. 34, pp. 2987–2990 (1976).
Paaren et al., Proc. Nat'l. Acad. Sci. USA, vol. 75, No. 5, pp. 2080–2081 (1978).
Esvelt et al., J. Org. Chem., vol. 46, pp. 556–558 (1981).
Paaren et al., Proc. Nat'l. Acad. Sci. USA, vol. 78, No. 10, pp. 6173–6175 (1981).
Morrison and Boyd, *Organic Chemistry*, 3d ed., Allyn & Bacon, Boston 1973, p. 458.

*Primary Examiner*—Leonard Schenkman
*Assistant Examiner*—Joseph A. Lipovsky
*Attorney, Agent, or Firm*—Saidman, Sterne, Kessler & Goldstein

[57] ABSTRACT

Novel synthetic derivatives of vitamin D compounds are disclosed as well as processes for their synthesis. The novel compounds are 1-alpha-thio and acylated, 1-beta-thio derivatives of vitamin D compounds and the glycosylated, hydroxylated, fluorinated, and glycosylated orthoester analogues thereof.

17 Claims, 4 Drawing Figures

BIOLOGICALLY ACTIVE 1-THIO DERIVATIVES OF VITAMIN D

BACKGROUND OF THE INVENTION

1. Field of the Invention

This invention is directed to synthetic vitamin D derivatives which are characterized by 1-thio substitution, these vitamin D derivatives demonstrating biological activity. Included in the invention is the process for producing the biologically active vitamin D derivatives as well.

2. Brief Description of Background Art

The chemistry, biochemistry, physiology, and metabolism of vitamin D are well described by Holick et al., *Harrison's PRINCIPLES OF INTERNAL MEDICINE*, 10th Edition (1983), McGraw-Hill Book Company, New York, pages 1944–1948. Vitamin D is actually a hormone rather than a vitamin, and is a derivative of a cutaneous steroid precursor, 7-dehydrocholesterol (provitamin $D_3$). Upon exposure to ultraviolet radiation, the precursor undergoes a photochemical reaction resulting in the cleavage of a C—C bond between $C_9$ and $C_{10}$, thereby generating a 9,10-secosteroid (previtamin $D_3$). Previtamin $D_3$ is a thermally labile intermediate, the compound undergoing molecular arrangement involving its conjugated triene system to a thermally stable 9,10-secosteroid, vitamin $D_3$.

Vitamin $D_2$ differs from vitamin $D_3$ in that it contains a double bond between $C_{22}$ and $C_{23}$ and further contains a $C_{24}$-methyl group. And while vitamin $D_3$ is the only endogenous form of vitamin D in human skin, both vitamins $D_2$ and $D_3$ are metabolized identically and have equivalent biological potency in most mammals. Vitamin $D_4$ has a single bond between $C_{22}$ and $C_{23}$ and contains a methyl group at $C_{24}$. As is generally understood, for the purposes of this disclosure, the term "vitamin D" is intended to include vitamin $D_2$, vitamin $D_3$, and vitamin $D_4$.

Upon exposure to sunlight, the ultraviolet radiation energy between wavelengths 290–320 nm results in the photochemical conversion of 7-dehydrocholesterol (provitamin $D_3$) stored in the epidermal layer to previtamin $D_3$. Previtamin $D_3$ slowly converts to vitamin $D_3$ by a temperature-dependent process that takes approximately 48 hours. Once vitamin D enters the circulation, either by its absorption in the small intestine from the diet or through the skin, it is transported through the circulation by a specific transport protein, an alpha globulin, to the liver for its hydroxylation.

In the liver, vitamin D is metabolized to 25-hydroxyvitamin D by various vitamin D-25-hydroxylases, with 25-hydroxyvitamin D being one of the major circulating metabolites of vitamin D.

25-hydroxyvitamin D is not considered to be biologically active at physiological levels in vivo. After formation in the liver, 25-hydroxyvitamin D is bound by the high-affinity vitamin D-binding protein of plasma and is transported to the kidney for an additional stereospecific hydroxylation on either $C_1$ or $C_{24}$, the kidney playing a pivotal role in the metabolism of 25-hydroxyvitamin D to biologically active metabolites.

It is now recognized that the 1-alpha-hydroxy group is important in the binding of 1,25-dihydroxy vitamin $D_3$ with its intestinal cytosolic receptor and in the expression of its calcium-transport activity (Norman, A. W., *Vitamin D, Basic and Clinical Nutrition*, Marcel Dekker, Inc., Vol. 2, 224–231 (1980); Franceschi, R. T. et al., *Arch. Biochem. Biophys.* 210, 1 (1981)).

1-alpha,25-dihydroxyvitamin $D_3$ has been established as the hormonally active form of vitamin $D_3$ (DeLuca, H. F. et al., *Annu. Rev. Biochem.* 45, 631 (1976); Norman, A. W. et al., *Endocrin. Rev.* 3, 331 (1982)). The 1-alpha, 25-dihydroxyvitamin D is taken up in the intestine by specific cytoplasmic receptor proteins to stimulate calcium and phosphate transport from the intestinal lumen into the circulation. Vitamin $D_3$ deficiency, or disturbances in the metabolism of vitamin $D_3$ cause such diseases as rickets, renal osteodystrophy and related bone diseases, as well as, generally, hypo- and hypercalcemic states. Thus, biologically active forms of vitamin $D_3$ are crucial in maintaining normal development of bone structure by regulating blood calcium levels.

Inadequate endogenous production of vitamin $D_3$ in the skin, insufficient dietary supplementation and/or the inability of the small intestine to absorb adequate amounts of vitamin D from the diet may cause hypovitaminosis D. Disease states which are equivalent to hypovitaminosis D are caused by drugs that antagonize vitamin D action, alteration in the metabolism of vitamin D, or inadequate response of tissue receptors to vitamin D metabolites. Hypovitaminosis D or equivalent disease states result in disturbances in the mineral ion metabolism and PTH secretion and mineralization defects in the skeleton such as rickets in children and osteomalacia in adults. As may be expected, adjunct therapy for hypovitaminosis D includes administration of vitamin $D_2$, vitamin $D_3$ or their metabolites which are hydroxylated at positions 1; 1,25; 1,24,25; 24,25; 25,26; or 1,25,26. However, these compounds are water insoluble, rendering post-administration dissolution in the gastrointestinal lumen as the rate-limiting step in drug absorption. As is disclosed in U.S. Pat. No. 4,410,515 to Holick, Sally A. et al., a form of vitamin D now exists which is hydrophilic and/or water-soluble, yet preserves the normal biological properties of the water-insoluble drug. These compounds, vitamin D glycosides, are derivatives of vitamin D which are characterized by the presence of a straight or branched chain glycosidic residue containing 1–20 glycoside units per residue substituted at the $C_1$, $C_{24}$, $C_{25}$, and/or $C_{26}$ positions. These vitamin D glycosides and their methods of production are fully disclosed in the aforementioned U.S. Pat. No. 4,410,515, the entire disclosure of which is incorporated by reference herein.

Alternative methods for the solubilization of vitamin D derivatives include conjugating compounds to glycosyl orthoester residues, as disclosed in co-pending U.S. patent application Ser. No. 607,117 of Holick et al., filed May 3, 1984, and U.S. patent application Ser. No. 667,813 to Holick et al., filed Nov. 2, 1984, both applications incorporated by reference herein.

Other derivatives of vitamin D are known as well, wherein the compounds contain a 5,6-epoxy (described in *Jpn. Kokai Tokkyo Koho* JP 58,216,178 [83,216,178], Dec. 15, 1983) and fluoro derivatives (the production of which is described in Shiina, et al., *Arch. Biochem. Biophys.* 220, 90 (1983)) and are further incorporated by reference herein.

It has also previously been reported that replacement of the 3-beta-hydroxy of vitamin $D_3$ with a thio group has made the vitamin biologically inert (Bernstein, S. et al., *J. Organ. Chem.*, 16, 685 (1951). 1-fluoro vitamin $D_3$ has been synthesized and shown to possess biological activity, possibly as a result of 25-hydroxylation (Napoli, J. L. et al., *Biochemistry* 18, 1641 (1979)). However, 1-alpha-25-difluoro vitamin $D_3$ has been found to be biologically inert (Paaren, H. E. et al., *Arch. Biochem. Biophys.* 209, 579 (1981)).

However, prior to the present, vitamin D derivatives containing 1-thio substitution and demonstrating biological activity have not been reported.

SUMMARY OF THE INVENTION

Knowing that the 1-alpha-hydroxy group plays a critical role in the binding of 1,25-dihydroxyvitamin $D_3$ with its intestinal cytosolic receptor and in the expression of calcium transport activity of the compound, the investigators undertook to evaluate the effect of a group other than the 1-hydroxyl on the biological activity of the vitamin D hormone. Accordingly, the 1-thiovitamin D compounds of this invention resulted.

In order to evaluate these novel 1-thio compounds, it was necessary as well to develop a synthetic process for their production. The following disclosure describes the compounds and their process of production.

The biologically active 1-thio derivatives of vitamin D of this invention have the following general formula (I):

wherein:
(1) R is epoxy or double bond;
(2) $R^1$ is H, an acyl residue or a straight or branched chain glycosidic residue containing 1–20 glycosidic units per residue, or $R^1$ is an orthoester glycoside moiety of the formula (II):

in which in said formula (II)
(a) A represents a glucofuranosyl or glucopyranosyl ring,
(b) $R^2$ is hydrogen, lower alkyl, aralkyl or aryl, and
(c) $R^3$ is hydrogen or a straight or branched chain glycosidic residue containing 1–20 glyosidic units per residue;
(3) the bond between $C_{22}$ and $C_{23}$ is single or double;
(4) Y is hydrogen, fluorine, methyl or ethyl;
(5) Z is hydrogen, fluorine or $OR^1$, where $R^1$ is as defined above;
(6) X is hydrogen, or $OR^1$, wherein $R^1$ is as defined above;
(7) $Q^a$ is $CH_3$, $CF_3$, or $CH_2OR^1$, with $OR^1$ as defined above; and
(8) $Q^b$ is $CF_3$ or $CH_3$;
with the proviso that when Y is fluorine, Z is not OH, said compound being biologically active.

DESCRIPTION OF THE PREFERRED EMBODIMENTS

This invention provides for the first time synthetic 1-thio substituted vitamin D compounds as well as acylated hydroxylated, fluorinated, epoxydated, glycosylated, and orthoester glycosylated derivatives thereof.

The compounds of the invention are those having the formula (I):

wherein:
(1) R is epoxy or double bond;
(2) $R^1$ is H, an acyl residue, or a straight or branched chain glycosidic residue containing 1–20 glycosidic units per residue, or $R^1$ is an orthoester glycoside moiety of the formula (II)

in which in said formula (II)
(a) A represents a glucofuranosyl or glucopyranosyl ring,
(b) $R^2$ is hydrogen, lower alkyl, aralkyl or aryl, and
(c) $R^3$ is hydrogen or a straight or branched chain glycosidic residue containing 1–20 glyosidic units per residue;
(3) the bond between $C_{22}$ and $C_{23}$ is single or double;
(4) Y is hydrogen, fluorine, methyl or ethyl;
(5) Z is hydrogen, fluorine or $OR^1$, where $R^1$ is as defined above;
(6) X is hydrogen, or $OR^1$, wherein $R^1$ is as defined above;
(7) $Q^a$ is $CH_3$, $CF_3$, or $CH_2OR^1$; and
(8) $Q^b$ is $CF_3$ or $CH_3$;
with the proviso that when Y is fluorine, Z is not OH, said compound being biologically active.

The stereochemistry at position 1 may be alpha (out of the plane of the paper) or beta (into the plane).

Of particular interest are compounds according to formula (I) above wherein R is a double bond, $R^1$ is hydrogen, the bond between $C_{22}$ and $C_{23}$ is single or double, Y is hydrogen or methyl, Z is hydrogen, $Q^a$ and $Q^b$ are each methyl, and X is hydrogen or hydroxy. These compounds have the general formula (III):

in which said formula $R^4$ is hydrogen or hydroxy, $R^5$ is hydrogen or methyl, and the bond between $C_{22}$ and $C_{23}$ is single or double. These compounds are the 1-alpha- and 1-beta-thio-substituted derivatives of vitamin $D_2$, vitamin $D_3$, vitamin $D_4$, 25-hydroxyvitamin $D_2$, 25-hydroxyvitamin $D_3$, and 25-hydroxy vitamin $D_4$. Of special interest are the compounds of formula (III) wherein the bond between $C_{22}$ and $C_{23}$ is single, $R^5$ is hydrogen, and $R^4$ is hydrogen or hydroxy. These compounds are, respectively 1-thiovitamin $D_3$ and 1-thio-25-hydroxyvitamin $D_3$, both the 1-alpha and 1-beta configured compounds.

The synthesis of the compounds of the above formula (III) wherein the —SH moiety is in the beta configuration proceeds as follows. The starting materials are compounds which are 1-alpha-hydroxy-(6R)-methoxycyclo derivatives of vitamin D and 25-hydroxyvitamin D, having the general formula (IV):

M is defined by residues having the following structural configuration (V):

In formula (V), the bond between $C_{22}$ and $C_{23}$ is single or double, $R^5$ is hydrogen or methyl, and $R^4$ is hydrogen or hydroxy (where the bond between $C_{22}$ and $C_{23}$ is single and $R^5$ is hydrogen, the compounds are derivatives of vitamin $D_3$, where the bond between $C_{22}$ and $C_{23}$ is double and $R^5$ is methyl, the compounds are derivatives of vitamin $D_2$, and where the bond between $C_{22}$ and $C_{23}$ is single and $R^5$ is methyl, the compounds are derivatives of vitamin $D_4$).

The starting point in the synthesis, compound IV may be prepared by selenium dioxide oxidation of the (6R)-methoxy-3,5-cyclovitamin D precursor according to the procedure of Paaren, H. P. E. et al., *Proc. Natl. Acad. Sci. USA*, 75, 2080 (1978).

Compound IV is reacted with thioacetic acid in a suitable solvent, typically tetrahydrofuran (THF), in the presence of triphenylphosphine. After stirring at room temperature, diethylazodicarboxylate (DAD) is added, with continued stirring, resulting in the formation of 1-beta-thioacetoxy-(6R)-methoxycyclo-vitamin D having the following general formula (VI):

where Ac is the acetyl radical ($CH_3CO$).

Cycloreversion of the compounds of formula VI in acetic acid yield the 1-beta-thioacetoxy-3-acetoxy-derivatives, said derivatives having the general formula (VII)

The 1-beta-thioacetoxy-3-acetoxy may be carefully hydrolyzed under an inert atmosphere, typically using 4% potassium hydroxide in methanol for the hydrolysis, followed by acidification with acetic acid and purification by reverse phase HPLC, to yield the final product, said product having the general formula (III) above, where the —SH is in the beta configuration.

The synthesis of the compounds of the above formula (III) wherein the —SH moiety is in the alpha configuration proceeds as follows in a similar fashion. The starting materials are compounds which are 1-beta-hydroxy-(6R)-methoxycyclo derivatives of vitamin D and 25-hydroxyvitamin D, having the general formula (VIII):

M being defined as above.

The synthesis of the 1-beta-hydroxy-methoxycyclo compounds (VIII) proceeds with the 1-alpha-hydroxymethoxycyclo derivatives (IV), formed according to Paaren, H. P. E. et al., supra, as the starting point. The synthesis of 1-beta-hydroxy-(6R)-methoxycyclovitamin $D_3$ is described in detail below at Example 7. In general, starting compound IV is reacted with triphenylphosphine and p-nitrobenzoic acid, with a subsequent addition of diethylazodicarboxylate ester, yielding both the 1-alpha- and 1-beta-(p-nitrobenzoyloxy)-(6R)-methoxycyclovitamin D compounds. See Loibner et al., *Tetrahedron*, 34: 713 (1978). The 1-beta compound, after separation by TLC, may be reacted with ether-methanol containing a base to yield the 1-beta-hydroxy-6R-methoxycyclovitamin D compound (VIII).

Compound VIII is reacted with thioacetic acid in a suitable solvent, typically THF in the presence of triphenylphosphine. After stirring at room temperature, DAD is added, with continued stirring, resulting in the formation of 1-alpha-thioacetoxy-(6R)-methoxycyclovitamin D having the following general formula (IX):

where Ac is the acetyl radical ($CH_3CO$).

Thus, as may be seen by the synthetic procedures for the 1-alpha- and 1-beta-thio derivatives of vitamin D, esterification using triphenylphosphine and DAD proceeds with inversion of configuration and without allylic rearrangement, as reported by Loibner et al., *Tetrahedron*, 34: 713 (1978) and Grynkiewicz et al., *Tetrahedron*, 32: 2109 (1976).

Cycloreversion of the compounds of formula IX in acetic acid yield the 1-alpha-thioacetoxy-3-acetoxy-derivatives, said derivatives having the general formula (X):

The 1-alpha-thioacetoxy-3-acetoxy derivatives may be carefully hydrolyzed under an inert atmosphere, typically using 4% potassium hydroxide in methanol for the hydrolysis, followed by acidification with acetic acid and purification by reverse phase HPLC, to yield the final product, said product having the general formula (III) above, where the —SH is in the alpha configuration.

Another synthesis of the 1-beta-configured compounds of the above formula (III) proceeds as follows. The starting materials are compounds which are 1-alpha-hydroxy-(6R)-methoxycyclo derivatives of vitamin D and 25-hydroxy vitamin D, having the general formula (IV), defined as above:

M is defined as above in formula V.

Compound IV is reacted with methanesulfonyl chloride in a suitable solvent, typically pyridine, at low temperatures, typically 0° C. The reaction product, the corresponding mesylates, are produced in quantitative yield and have the following formula (XI):

where Ms is the mesylate radical (methanesulfonyl).

Treatment of compounds XI with an excess of potassium thioacetate, typically a 20-fold excess of the thioacetate in dry DMSO at approximately ambient temperature yields the 1-beta-thio acetoxy reaction products having the formula (VI) as above:

Cycloreversion of the compounds of formula VI in acetic acid yield the 1-beta-thioacetoxy-3-acetoxy-derivatives, said derivatives having the general formula (VII) as above:

(VII)

The 1-beta-thioacetoxy-3-acetoxy derivatives may be carefully hydrolyzed under an inert atmosphere, typically using 4% potassium hydroxide in methanol for the hydrolysis, followed by acidification with acetic acid and purification by reverse phase HPLC, to yield the final product, said product having the general formula (III) above, with the —SH moiety in the beta configuration.

Utilizing the procedure of Eisman, J. et al., *Steroids*, Vol. 30, 245–257 (1977)), it was shown that 1-beta-thio-25-hydroxyvitamin $D_3$ *1 is able to compete with* $^3H$-1,25-dihydroxyvitamin $D_3$ for 1,25-dihydroxyvitamin receptor site. As may be seen from FIG. 3, the 1-beta-thio compound (Δ) is about 200 times less active than the 1-alpha-25-dihydroxy compound. DeLuca, H. F. et al., *Nutrition Reviews*, Vol. 37, No. 6, at page 183 (1979), has suggested that recognition by the receptor site indicates analogue activity. Thus, the 1-beta-thio-25-hydroxyvitamin $D_3$ can be used as a biologically active analogue of the natural compound.

To confirm this, the effects of various compounds on cell proliferation rates were studied, using human fibroblasts to evaluate activity. The results are reported in FIG. 4. Human fibroblasts were prepared as described by Clemens, *J. Clin. Endocrinol. Met.*, 56: 197 (1983). In the study, $2.5 \times 10^5$ cells, in quadruplicate, were exposed to (a) 95% ethanol (■); (b) ethanol plus 1-alpha-25-dihydroxyvitamin $D_3$ (□); or (c) 1-beta-thio-25-hydroxyvitamin $D_3$ plus 1-alpha, 25-dihydroxyvitamin $D_3$ (●). As may be seen from FIG. 4, the 1-alpha-25-dihydroxyvitamin $D_3$ inhibited cell generation by about 30% (□). The addition of the 1-beta-thio compound to the 1-alpha,25-dihydroxy compound blocked the inhibitory effect of the latter compound (●). This result indicates antagonistic properties for the 1-thio compound. Further, the 1-thio compound alone had no effect on cell generation time (data not shown).

Figure 3:
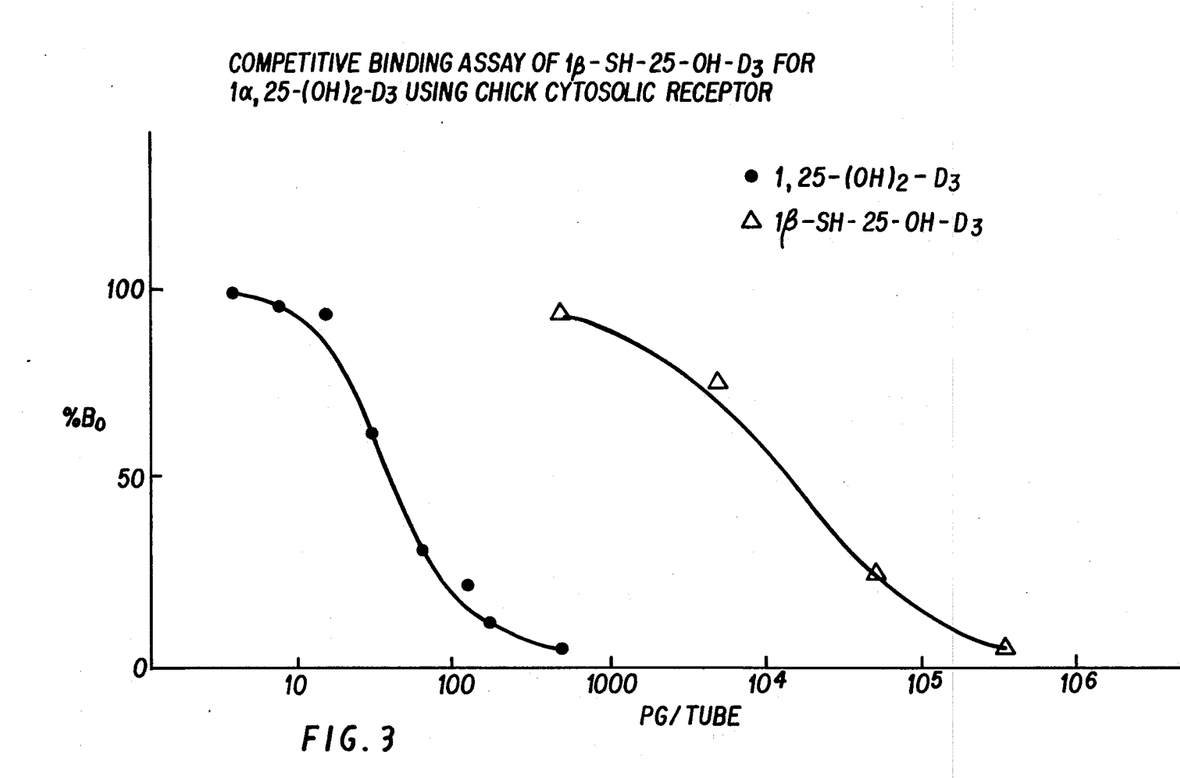
FIG. 3 is a graph comparing the binding characteristics of 1-alpha,25-dihydroxyvitamin $D_3$ (●) and 1-beta-thio-25-hydroxyvitamin $D_3$ (△) using chick cytosolic receptor.
Figure 4:
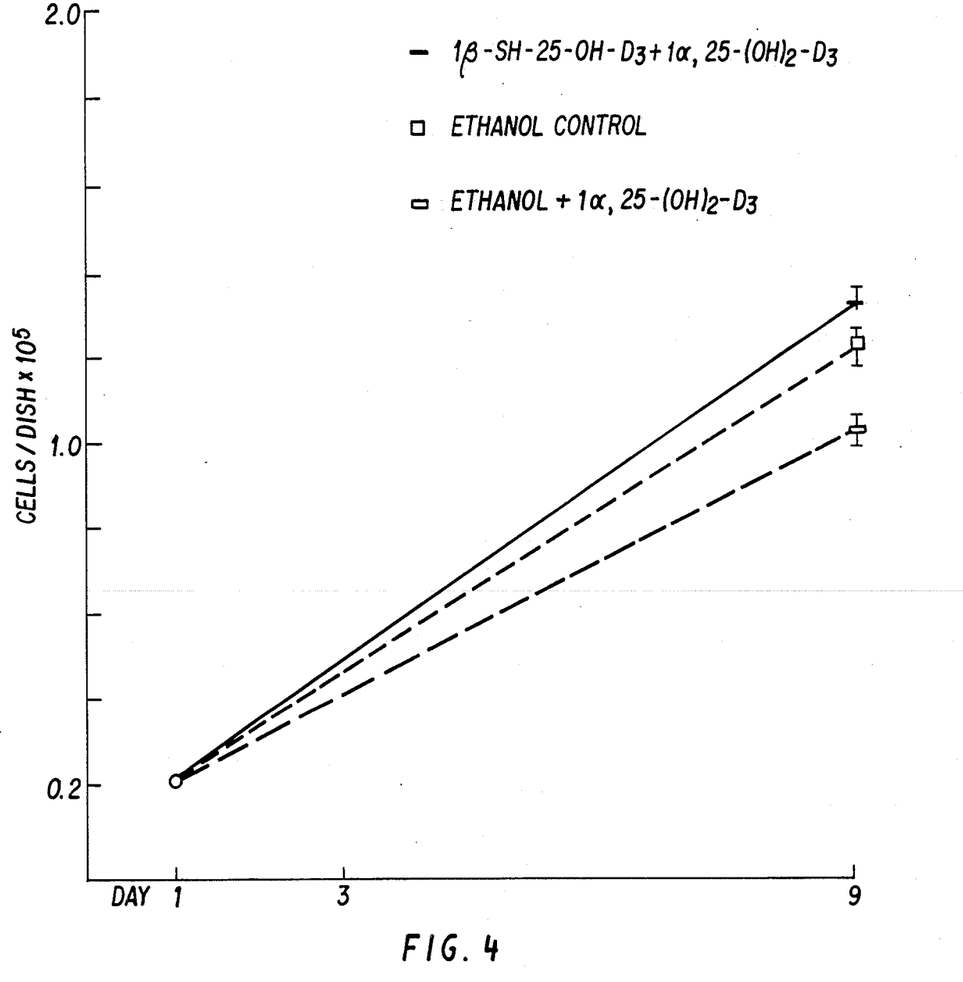
FIG. 4 is a graph comparing the effects of ethanol (■), ethanol plus 1-alpha,25-dihydroxyvitamin $D_3$ (□), and 1-beta-thio-25-hydroxyvitamin $D_3$ and 1-alpha,25-dihydroxyvitamin $D_3$ (■) on human fibroblast cell proliferation.

Based on FIGS. 3 and 4, it may be seen that 1-beta-thio-hydrovitamin $D_3$ is recognized by the cytosol receptor site which recognizes the 1,25-dihydroxy compound, and blocks the ability of the 1,25-dihydroxy compound from affecting in vitro fibroblast cell division.

It is also known (DeLuca, supra, page 183) that in chick intestine cytosol receptor binding specificity studies that 1-beta,25-dihydroxyvitamin $D_3$ is 3,000 times less active than 1-alpha,25-dihydroxyvitamin $D_3$ for the 1,25-dihydroxyvitamin $D_3$ receptor site. Replacement of the beta-hydroxy with beta-thio results in a compound which is only 200 times less active, a 15-fold increase in cytosol receptor binding activity. In like manner, replacement of the 1-alpha-hydroxy with 1-alpha-thio is expected to bind to the receptor more avidly. Thus, the 1-alpha-thio compounds will have biological activity as agonists and/or antagonists for their 1-alpha-hydroxy counterparts.

As agonists, the compounds have clinical utility for treating vitamin D-deficient diseases such as acquired and inherited disorders of 25-hydroxyvitamin D metabolism (e.g. chronic renal failure, hypoparathyroidism, and vitamin D-dependent rickets Type I), hypeproliferative skin disorders such as psoriasis, and tumors which possess receptors for 1,25-dihydroxyvitamin $D_3$.

As antagonists, the compounds have utility as therapeutic agents for the treatment of hypercalcemia and hypercalciuria due to elevated levels of 1,25-dihydroxyvitamin $D_3$, including sarcoidosis, hyperparathyroidism, idiopathic hypercalciuria and tumor hypercalcemia.

One group of compounds having the general formula (I) above are the glycosidic and/or hydroxylated derivatives thereof. Referring to formula (I), these compounds are characterized by $R^1$ being hydrogen, acyl, or a straight or branched chain glycosidic residue containing 1–20 glycosidic units per residue.

By glycosidic units are meant glycopyranosyl or glycofuranosyl, as well as their amino sugar derivatives. The residues may be homopolymers, random or alternating, or block copolymers thereof. The glycosidic units have free hydroxy groups, or hydroxy groups acylated with a group wherein $R^8$ is hydrogen, lower alkyl, aryl or aralkyl. Preferably $R^8$ is $C_1$–$C_6$ alkyl, most preferably acetyl or propionyl; phenyl, nitrophenyl, halophenyl, lower alkyl-substituted phenyl, lower alkoxy substituted phenyl, and the like; or benzyl, nitrobenzyl, halobenzyl, lower alkyl-substituted benzyl, lower alkoxy-substituted benzyl, and the like.

The glycosylated compounds of the invention contain at least one glycosidic residue at positions 1, 3, 24, 25 or 26. They may, however, contain more than one, and up to five such glycosidic residues simultaneously. Preferred are those compounds derived from 1-alpha- or 1-beta-thiovitamins $D_4$, $D_3$, or $D_2$; 1-alpha- or 1-beta-thio-25-hydroxy vitamins, $D_4$, $D_3$, or $D_2$; 1-alpha- or 1-beta-thio-24,25-dihydroxy-vitamins $D_4$, $D_3$ or $D_2$; and 1-alpha- or 1-beta-thio-25,26-dihydroxy vitamins $D_3$ or $D_2$. Most preferred among these are the 1-alpha-thio and 1-beta-thio derivatives of vitamins $D_3$ or $D_2$; and 25 hydroxyvitamin $D_3$ or $D_2$, with the $D_3$ derivatives of highest priority.

In the case of multihydroxylated forms of the vitamins (e.g.: 1-thio-25-hydroxy-vitamin $D_3$ has two hydroxy groups, at positions 3 and 25), the preferred compounds of the invention are those wherein less than all of the multiple hydroxy groups are acylated glycosylated, most preferably those where only one of the multiple hydroxy groups is acylated or glycosylated. Further, the thio group at the 1 position may be glycosylated as well.

The glycosides can comprise up to 20 glycosidic units. Preferred, however, are those having less than 10, most preferred, those having 3 or less than 3 glycosidic units. Specific examples are those containing 1 or 2 glycosidic units in the glycoside residue.

The glycopyranose or glycofuranose rings or amino derivatives thereof may be fully or partially acylated or completely deacylated. The completely or partially acylated glycosides are useful as defined intermediates for the synthesis of the deacylated materials.

Among the possible plycopyranosyl structures are glucose, mannose, galactose, gulose, allose, altrose, idose, or talose. Among the furanosyl structures, the preferred ones are those derived from fructose, arabinose or xylose. Among preferred diglycosides are sucrose, cellobiose, maltose, lactose, trehalose, gentiobiose, and melibiose. Among the triglycosides, the preferred ones may be raffinose or gentianose. Among the amino derivatives are N-acetyl-D-galactosamine, N-acetyl-D-glucosamine, N-acetyl-D-mannosamine, N-acetylneuraminic acid, D-glucosamine, lyxosylamine, D-galactosamine, and the like.

When more than one glycosidic unit is present on a single hydroxy group or the 1-thio group (i.e., di or polyglycosidic residues), the individual glycosidic rings may be bonded by 1-1, 1-2, 1-3, 1-4, 1-5 or 1-6 bonds, most preferably 1-2, 1-4 and 1-6. The linkages between individual glycosidic rings may be alpha or beta.

The configuration of the thio linkage of the glycosidic residue attached to the 1-thiovitamin D molecule may be either alpha (into the plane of the paper) or beta (out of the plane of the paper). It is preferred if the configuration of the 3-hydroxy or glycosidoxy group at $C_3$ be beta, and that, independently or simultaneously the configuration of the glycosyl residue at $C_1$ be alpha. It is also preferred that the configuration around $C_{24}$ be R. When, at $C_{24}$, X=H and $R^2$=$CH_3$ or $CH_2CH_3$, the configuration at $C_{24}$ is preferably S.

Specific examples of compounds of the invention are the following 1-alpha-thio derivatives:
1-alpha-thio-vitamin $D_3$, beta-(beta-D-glucopyranoside);
1-alpha-thio-vitamin $D_3$, beta-(beta-D-fructofuranoside);
1-alpha-thio-vitamin $D_3$, beta-(beta-D-cellobioside);
1-alpha-thio-3-beta-(beta-maaltosyl) vitamin $D_3$;
1-alpha-thio-3-beta-raffinosyl-vitamin $D_3$;
1-alpha-thio-3-beta-gentiobiosyl-vitamin $D_3$;
1-alpha-thio-(beta-D-glucopyranosyl)-vitamin $D_3$;
1-alpha-thio-(beta-D-fructofuranosyl)-vitamin $D_3$;
1-alpha-thio-(beta-D-cellobiosyl)-vitamin $D_3$;
1-alpha-thio-(beta-D-maltosyl)-vitamin $D_3$;
1-alpha-thio-(beta-D-lactosyl)-vitamin $D_3$;
1-alpha-thio-(beta-D-trehalosyl)-vitamin $D_3$;
1-alpha-thio-raffinosyl-vitamin $D_3$;
1-alpha-thio-gentiobiosyl-vitamin $D_3$;
1-alpha-thio-25-hydroxy-vitamin $D_3$; 3-beta-(beta-D-fructofuranoside);
1-alpha-thio-25-hydroxy vitamin $D_3$, 3-beta-(beta-D-glucopyranoside);
1-alpha-thio-(beta-D-glycopyranosyl)-25-hydroxy-vitamin $D_3$;
1-alpha-thio-(beta-D-fructofuranosyl)-25-hydroxy-vitamin $D_3$;
1alpha-thio-(beta-D-fructofuranosyl)-vitamin $D_3$;
1-alpha-thio-25-(beta-cellobiosyl)-vitamin $D_3$;
1-alpha-thio-25-(beta-maltosyl)-vitamin $D_3$;
1-alpha-thio-25-(beta-lactosyl)-vitamin $D_3$;
1-alpha-thio-25-(beta-trehalosyl)-vitamin $D_3$;
1-alpha-thio-25-raffinosyl-vitamin $D_3$;
1-alpha-thio-25-gentiobiosyl-vitamin $D_3$.

Other specific examples include the following 1-beta-thio derivatives:
1beta-thio-vitamin $D_3$, beta-(beta-D-glucopyranoside);
1-beta-thio-vitamin $D_3$, beta-(beta-D-fructofuranoside);
1-beta-thio-vitamin $D_3$, beta-(beta-D-cellobioside);
1-beta-thio-3-beta-(beta-maltosyl) vitamin $D_3$;
1-beta-thio-3-beta-raffinosyl-vitamin $D_3$;
1-beta-thio-3-beta-gentiobiosyl-vitamin $D_3$;
1-beta-thio-(beta-D-glucopyranosyl)-vitamin $D_3$;
1-beta-thio-(beta-D-fructofuranosyl)-vitamin $D_3$;
1-beta-thio-(beta-D-cellobiosyl)-vitamin $D_3$;
1-beta-thio-(beta-D-maltosyl)-vitamin $D_3$;
1-beta-thio-(beta-D-lactosyl)-vitamin $D_3$;
1-beta-thio-(beta-D-trehalosyl)-vitamin $D_3$;
1-beta-thio-raffinosyl-vitamin $D_3$;
1-beta-thio-gentiobiosyl-vitamin $D_3$;
1-beta-thio-25-hydroxy-vitamin $D_3$, 3-beta-(beta-D-fructofuranoside);
1-beta-thio-25-hydroxy vitamin $D_3$, 3-beta-(beta-D-glucopyranoside);
1-beta-thio-(beta-D-glycopyranosyl)-25-hydroxy-vitamin $D_3$;
1-beta-thio-(beta-D-fructofuranosyl)-25-hydroxy-vitamin $D_3$;
1-beta-thio-(beta-D-fructofuranosyl)-vitamin $D_3$;
1-beta-thio-25-(beta-cellobiosyl)-vitamin $D_3$;
1-beta-thio-25-(beta-maltosyl)-vitamin $D_3$;
1-beta-thio-25-(beta-lactosyl)-vitamin $D_3$;
1-beta-thio-25-(beta-trehalosyl)-vitamin $D_3$;
1-beta-thio-25-raffinosyl-vitamin $D_3$;
1-beta-thio-25-gentiobiosyl-vitamin $D_3$.

All of the aforementioned derivatives can also be prepared with vitamin $D_2$ and vitamin $D_4$.

The glycosidic derivatives of the 1-thio-vitamins D of the present invention can be prepared by standard synthetic methods well known to those skilled in the art. These methods depend on whether the starting B 1-thiovitamin D contains one or more hydroxy groups. When the vitamin contains only one hydroxy group, the syntheses are straightforward, since the monohydroxylated 1-thiovitamin D (hydroxylated at position 3) is treated with silver carbonate in a refluxing solution of an inert nonpolar solvent such as benzene or toluene, to which is added a fully acylated glycoside or fully acylated straight or branched chain glycosidic polymer, either of these containing an appropriate leaving group (L.G.) at position C-1, of the terminal ring (or on the single ring, as called for). Condensation occurs according to the following reaction, indicated here for a single glycoside for purpose of illustration only:

In this reaction sequence, $R^8$ is as defined previously, LG is a common leaving group such as bromine, chlorine, iodine, p-toluenesulfonyl, and the like, capable of being replaced in a bimolecular nucleophilic substitution reaction.

When the 1-thiovitamin D is reacted with a glycosidic polymer, one or more of the $OCOR^8$ groups in the glycopyranoside or glycofuranoside rings is replaced by a fully acylated glycosidic unit, with the proviso that the total number of glycosidic units not exceed 20.

The reaction is carried out at from room temperature to refluxing conditions for a period of 1–10 hours, and is thereafter cooled and filtered to remove the silver salt. The filtrate is dried and the inert solvent is evaporated. The resulting product can be purified by any of the standard modern purification methods such as high performance liquid chromatography, silicic acid chromatography, thin layer preparative chromatography, and the like. A mixture of two products is normally obtained, being the alpha an beta glycofuranosyl or glycopyranosyl derivatives at the point of ring attachment. These can normally be separated by the aforementioned chromatographic methods.

After separation of the individual products, the glycosidic residues are deacylated in base, such as sodium methoxide in methanol, or ammonia in methanol. Further purification by high performance chromatography is usually indicated to obtain the highly purifided product.

When the starting 1-thiovitamin D carries two hydroxy groups (such as in 1-thio-25-hydroxy vitamin $D_3$), one of these may need to be selectively protected with a protecting group which can be ultimately removed after the condensation, and before, during or after the deacylation of the glycosidic residues. The same is true if three or more hydroxy groups are present in the vitamin starting materials, and less than all of these require to be glycosylated.

The selective protection of hydroxy groups in the starting materials can be carried out by using standard protection and deprotection reactions, well known to those skilled in Organic Chemistry.

Because each of the hydroxyl groups on the 1-thiovitamin D molecule have different reactivities due to the fact that they are either primary (e.g., 26-OH), secondary (e.g., 24-OH, 3-beta-OH, etc.) or tertiary (e.g., 25-OH) hydroxyl functions, selectivity can be achieved. Furthermore, the 3-beta-OH has different reactivity than the 1-thio. A good example of these reactivities is illustrated in Holick et al., *Biochemistry:* 10, 2799, 1971, where it is shown that the trimethylsilyl ether derivative of 1,25-dihydroxy-$D_3$ can be hydrolyzed in HCl-MeOH under mild conditions to yield 3,25-disilyl ether, and 25-monosilyl ether derivatives of 1,25-dihydroxy-$D_3$. Furthermore, to obtain a 1-thio-25-hydroxy-$D_3$ whereby the 3 hydroxy and 1-thio are protected, the 25-mono-silyl ether derivative of 1-thio-25-hydroxy-$D_3$ can be acetylated to form the 1-thio-25-hydroxy-$D_3$-1,3-diacetyl-25-trimethyl silyl ether. Because the acetates are quite stable to acid hydrolysis, this derivative can be acid hydrolyzed to yield 1-thioacetoxy-3-acetoxy-25-hydroxyvitamin $D_3$. An alternative approach would simply be to acetylate 1-thio-25-hydroxy-$D_3$ in acetic anhydride in pyridine at room temperature for 24 to 48 h to yield 1-thioacetoxy-25-hydroxy-vitamin $D_3$-3-acetate.

For protecting the 25-hydroxyl group for 25-hydroxyvitamin $D_3$ the following can be done: 25-OH-$D_3$ can be completely acetylated in acetic anhydride and pyridine under refluxing conditions for 24 h. The 3-Ac can be selectively removed by saponification (KOH in 95% MeOH-water) at room temperature for 12 h.

Once the desired protected 1-thiovitamin D derivative is prepared, the same is reacted with silver carbonate or other compounds for coupling (as described, e.g., by Igarashi, K., in "Advances in Carbohydrate Chemistry and Biochemistry," Vol. 34, 243–283, or Warren, C. D. et al., *Carbohydrate Research*, 82: 71–83 (1980), and the glycosidic or polyglycosidic residue as above, followed by deacylation, deprotection and purification. Further details of synthetic procedures are disclosed in U.S. Pat. No. 4,410,515, and incorporated by reference herein.

Oligosaccharide intermediates can be prepared, for example, by the methods of Lemieux, R. U., *J. of Amer. Chem. Soc.* 97: 4063–4069 (1975); or Frechet, J. M. J., "Polymer-Supported Reactions in Organic Synthesis" (1980) 407–434, or Kennedy, J. F., *Carbohydrate Chemistry*, 7: 496–595 (1975).

Commercially available sugars include: (Pfanstiehl Laboratories, Inc.): pentoses, such as: D-arabinose, L-arabinose, D-lyxose, L-lyxose, D-ribose, D-xylose, L-xylose: hexoses, such as: dextroses, D-fructose, D-galactose, alpa-D-glucose, beta-D-glucose, L-glucose, levulose, D-mannose, L-mannose, L-sorbose; heptoses, such as: D-glucoheptose, D-mannoheptulose, sedoheptulosan; disaccharides, such as: cellobiose, 3-O-beta-D-galactopyranosyl-D-arabinose, gentiobiose, lactoses, alpha-lactulose, maltose, alpha-melibiose, sucrose, trehalose, turanose; trisaccharides, such as: melezitose, raffinose; tetrasaccharides, such as: stachyose; polysaccharides and derivatives, such as: arabic acid, chitan, chitosan, dextrin, cycl-dextrins, glycogen, inulin.

The water-soluble glycosylated 1-thiovitamin D conjugates of the invention include hydrophilic derivatives of good water solubility to derivatives of excellent water solubility. The advantage of the conjugates resides in their water-solubility and thus their ease of administration in aqueous media such as, for example, saline or aqueous buffers. This allows the utilization of these conjugates in such devices as vitamin D releasing in-line pumps, intravenous dispensation and the like.

Yet another subset of compounds within the general formula (I) above are those compounds which are characterized as orthoester glycosides of 1-thiovitamin D. Referring to formula (I), the compounds are further characterized in that $R^1$ is an orthoesterglycoside moiety having the general formula (II) as above, said formula (II) being characterized in that A represents a glucofuranosyl or glucopyranosyl ring, $R^2$ is hydrogen, lower ($C_1$-$C_6$) alkyl, aralkyl, or aryl, and $R^3$ is hydrogen or a straight or branched chain glycosidic residue containing 1-20 glycosidic units per residue, with the term "glycosidic units" being defined as above. The 1-thiovitamin D compounds containing glycosyl orothoester residues may be prepared in accordance with the disclosure of co-pending U.S. application Ser. No. 607,117, filed May 3, 1984, and incorporated by reference herein. The synthetic process differs essentially only in the starting material, in the case of the present invention the starting material being the 1-thiovitamin D compounds of this invention.

Similarly, the 5,6-epoxy derivatives of 1-thiovitamin D, those compounds of formula (I) wherein R is epoxy, may be obtained as described in *Jpn. Kokai tokkyo Koho* JP No. 58,216,178 [83,216,178], December 15, 1983, incorporated by reference herein.

The compounds can be employed in dosage forms such as tablets, capsules, powder packets or liquid solutions, suspensions or elixirs for oral administration, or sterile liquids for formulations such as solutions or suspensions for parenteral use or formulations for topical application. In such compositions, the active ingredient will ordinarily always be present in an amount of at least $1 \times 10^{-6}\%$ by wt. based upon the total weight of a composition, and not more than 90% by wt. Generally, a dosage of active ingredient compounds will be from about 0.1 ug to 1 mg per kg of body weight. Of course, the dosage administered will be dependent upon the age, health, and weight of the recipient, kind of concurrent treatment, if any, frequency of treatment, hydrophilicity of the compounds, and the nature of the effect desired. An inert pharmaceutically acceptable carrier is preferably used. Among such carriers are 95% ethanol, vegetable oils, propylene glycols, saline buffers, etc.

Having now generally described this invention, the same will be understood by reference to the following examples which are provided herein for purposes of illustration only and are not intended to be limiting unless otherwise specified.

EXAMPLE 1

Synthesis of 1-alpha-thiovitamin $D_3$

Figure 1:
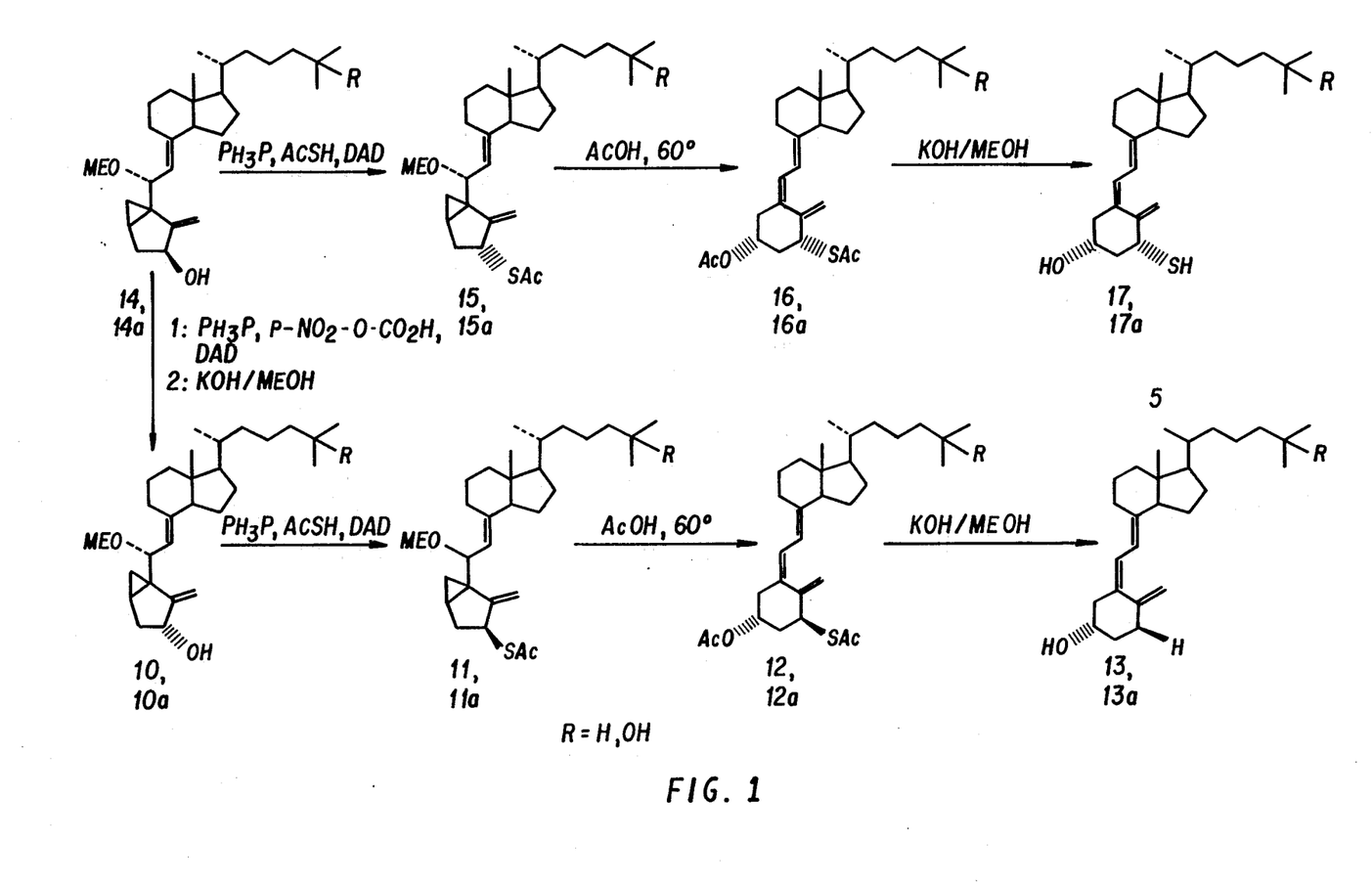
FIG. 1 is a schematic representation of a synthetic procedure for the production of 1-alpha- and 1-beta-thio-vitamin $D_3$ and the 25-hydroxy analogue of each, as well as a synthetic procedure for preparing 1-beta-hydroxy-(6R)-methoxycyclovitamin D compounds.

Referring to FIG. 1, with the numbers and letters in parentheses referring to the corresponding letters and numbers offset parenthetically in FIG. 1 for this example and Examples 2-4 which follow, thioacetic acid (5.4 mg, 5.1 ul) in dry THF (160 ul) is added to a stirred solution of 1-beta-hydroxy-(6R)-methoxycyclovitamin $D_3$ (10) (25.8 mg) and triphenylphosphine (22.0 mg) in absolute benzene (350 ul). The solution is stirred for five minutes at room temperature, diethylazodicarboxylate (DAD) (12.4 mg, 11.3 ul) in absolute benzene (45 ul) is added, and stirring continued overnight at room temperature. TLC indicates a mixture of 1-alpha-thioacetoxy-(6R)-methoxycyclovitamin $D_3$ (11) and unreacted starting material (10).

Treatment of (11) with warm acetic acid (55° C. for 15 minutes) yields 1-alpha-thioacetoxy-3-beta-acetoxyvitamin $D_3$ (12).

Careful hydrolysis (KOH-MeOH 5% w/v) of (12), under an inert atmosphere, followed by acidification with acetic acid yields 1-alpha-thiovitamin $D_3$ (13).

EXAMPLE 2

Synthesis of 1-alpha-thio-25-hydroxy-vitamin D

In similar fashion, using stoichiometrically equivalent amounts, thioacetic acid in dry THF is added to a stirred solution of 1-beta-25-dihydroxy-(6R)-methoxycyclovitamin $D_3$ (10a) and triphenylphosphine in absolute benzene. The solution is stirred for five minutes at room temperature, diethylazodicarboxylate in absolute benzene is added, and stirring continued overnight at room temperature. TLC indicates a mixture of 1-alpha-thioacetoxy-25-hydroxy-(6R)-methoxycyclovitamin $D_3$ (11a) and unreacted starting material (10a).

Treatment of (11a) with warm acetic acid yields 1-alpha-thioacetoxy-3-acetoxy-25-hydroxy-vitamin $D_3$ (12a).

Careful hydrolysis of (12a) with potassium hydroxide and methyl alcohol (under an inert atmosphere, followed by acidification with acetic acid, yields 1-alpha-thio-25-hydroxy-vitamin $D_3$ (13a).

EXAMPLE 3

Synthesis of 1-beta-thio-vitamin $D_3$

Thioacetic acid (4.9 mg, 4.6 ul) in dry THF (140 ul) is added to a stirred solution of 1-alpha-hydroxy-(6R)-methoxycyclovitamin $D_3$ (14) (23.3 mg) and triphenylphosphine (19.9 mg) in absolute benzene (300 ul). The solution is stirred for five minutes at room temperature, DAD (11.2 mg, 10.2 ul) in absolute benzene (40 ul) is added and stirring continued overnight at room temperature. TLC indicates a mixture of 1-beta-thioacetoxy-(6R)-methoxycyclovitamin $D_3$ (15) and unreacted starting material (14).

Treatment of (15) with warm acetic acid (55° for 15 minutes) yields 1-beta-thioacetoxy-3-beta-acetoxyvitamin $D_3$ (16).

Careful hydrolysis (KOH-MeOH 5% w/v) of (16), under an inert atmosphere followed by acidification with acetic acid, yields 1-beta-thio-vitamin $D_3$ (17).

EXAMPLE 4

Utilizing conditions and stoichiometrically equivalent amounts as set forth in Example 3 above, thioacetic acid in dry THF is added to a stirred solution of 1-alpha-25-dihydroxy-(6R)-methoxycyclovitamin $D_3$ (14a) and triphenylphosphine in absolute benzene. The solution is stirred for five minutes at room temperature, DAD in absolute benzene is added and stirring continued overnight at room temperature. TLC indicates a mixture of 1-beta-thioacetoxy-25-hydroxy-(6R)-methoxycyclovitamin $D_3$ (15a) and unreacted starting material (14a).

Treatment of (15a) with warm acetic acid (55° C. for 15 minutes) yields 1-beta-thioacetoxy-3-beta-acetoxy-25-hydroxy-vitamin $D_3$ (16a).

Careful hydrolysis of (16a) with potassium hydroxide-methyl alcohol (5% w/v), under an inert atmosphere, followed by acidification with acetic acid, yields 1-beta-thio-25-hydroxy vitamin $D_3$ (17a).

EXAMPLE 5

Synthesis and properties of 1-beta-thiovitamin $D_3$

Figure 2:
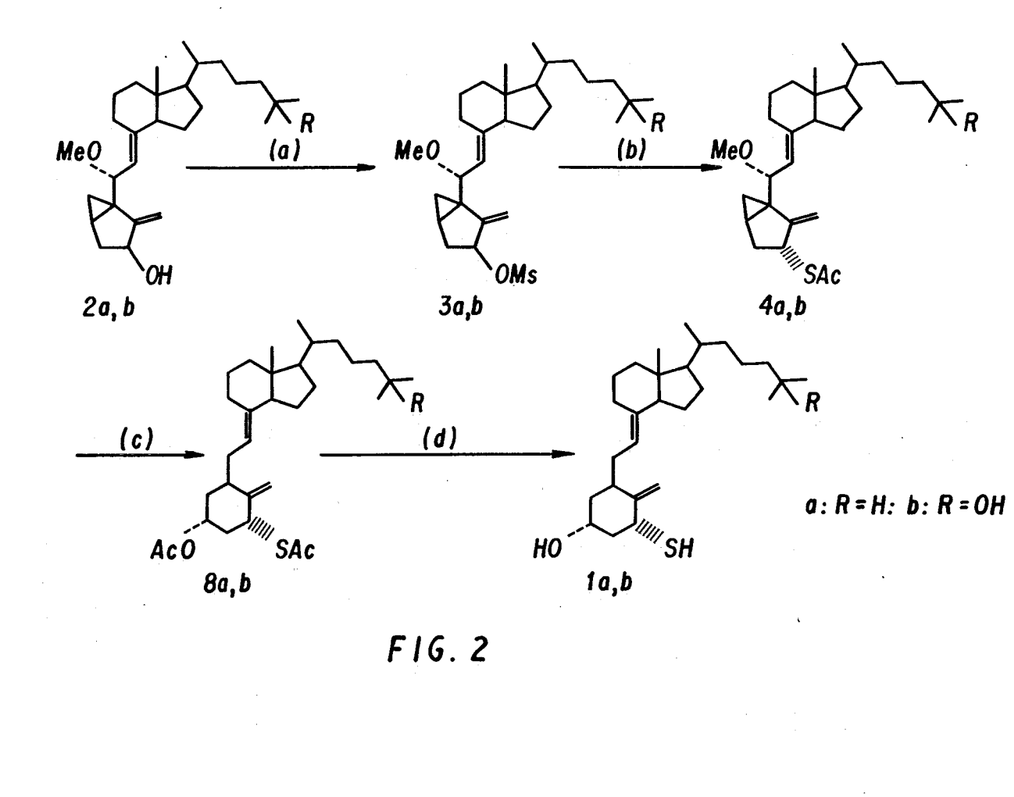
FIG. 2 is a schematic representation of another synthesis of the 1-beta-thiovitamin $D_3$ and 1-beta-thio-25-hydroxyvitamin $D_3$ compounds of this invention. This synthesis is described in Examples 5 and 6 below.

In the following example, the various structural formulae for the starting, intermediate, and final products are shown in FIG. 2. The numbers and letters in parenthesis refer to the corresponding letters and numbers offset parenthetically in FIG. 2.

1-alpha-hydroxy-(6R)-methoxycyclovitamin $D_3$(2a) was prepared by selenium dioxide oxidation of 3,5-cyclo-(6R)-methoxyvitamin $D_3$ utilizing the procedure of Paaren, H. P. E. et al., *Proc. Natl. Acad. Sci. Sci. USA*, 752,080 (1978). The resulting compound was reacted with methane sulfonyl chloride (1.1–2.0 eq) in pyridine at 0° C., the reaction yielding 1-alpha-methanesulfonyloxy-(6R)-methoxycyclovitamin $D_3$ (3a) in quantitative yield. Treatment of (3a) with a 20-fold excess of potassium thioacetate in dry DMSO at 20° C. exhibited both regio- and stereoselectivity, producing 1-beta-thioacetoxy-(6R)-methoxycyclovitamin $D_3$ (4a) (48% yield from 2a).

The $^1$H-NMR spectrum of (4a) contained peaks at $\delta$0.86(1H, m, H-4); $\delta$2.29(3H, s, SAc); $\delta$3.26(3H, s, OMe); $\delta$4.07(1H, d, $J_{6,7}$=9.1 Hz, H-6), $\delta$4.59(1H, d, J=9.0 Hz, H-1, $\delta$4.97(1H, d, $J_{7,6}$=9.1 Hz, H-7), $\delta$5.20(1H, bs, H-19Z), $\delta$5.29(1H, bs, H-19E).

Intermediate (4a) was typically non-UV absorbing at 254 nm. The IR spectrum of (4a) showed strong stretching absorptions at 1680 cm$^{-1}$(thioacetoxy C=O), and 1080 cm$^{-1}$ (ether C—O).

The NMR spectra (250 MHz $^1$H-NMR) were recorded from CDCl$_3$ solutions of the compound containing 0.1% TMS internal standard. All chemical shifts ($\delta$) are relative to that of TMS which is arbitrarily assigned the value of zero.

Cycloreversion of (4a) in acetic acid at 60° C. produced 1-beta-thioacetoxy-3-acetoxy-vitamin $D_3$ (8a) (40% yield) after separation from its 5,6-transisomer by TLC on silica gel. Stereochemical assignments at H-1 were based on comparison of the $^1$H-NMR spectra of 1-alpha-3-beta-diacetoxy vitamin D analogues of known (Paaren, H. P. E. et al., *Arch. Biochem. Biophys.*, 209, 579 (1981).

The $^1$H-NMR spectrum of (8a) was: $\delta$ 0.54(3H, s, H$_3$-18), $\delta$ 0.87(6H, d, $J_{25,26}$=6.7 Hz, H$_3$-26, H$_3$-27); $\delta$ 0.91(3H, d, $J_{20,21}$=6.1 Hz, H$_3$-21); $\delta$2.07(3H, s, OAc); $\delta$ 2.32(3H, s, SAc); $\delta$4.42(1H, m, H-1); $\delta$ 4.92(1H, bs, H-19Z); $\delta$ 5.04(1H, m, H-3); $\delta$5.36(1H, bs, H-19E), $\delta$ 5.91 and 6.33(1H, ABq, $J_{6,7}$=11 Hz, H-7 and H-6).

The UV spectrum of (8a) exhibited a broad $\lambda_{max}$ at 265 nm and a $\lambda_{min}$ at 228 nm characteristic of vitamin D.

The IR spectrum of (8a) contained strong stretch absorptions at 1725 cm$^{-1}$(acetoxy C=O), 1685 cm$^{-1}$(thioacetoxy C=O), and 1250 cm$^{-1}$(acetoxy C—O).

Careful hydrolysis (4% KOH in methanol) of (8a) under argon, followed by acidification with acetic acid and purification by reverse phase HPLC, furnished the final product (1a).

A broad $\lambda_{max}$ at 265 nm and $\lambda_{min}$ at 228 nm in the UV spectrum of (1a) was characteristic of vitamin D.

EXAMPLE 6

Synthesis and Properties of 1-beta-thio-25-hydroxyvitamin $D_3$

As in Example 1, the numbers and letters in parentheses refer to compounds, the structural formulas of which are shown in FIG. 2.

1-alpha,25-dihyroxycyclovitamin $D_3$, prepared by selenium dioxide oxidation of 25-hydroxy-3,5-cyclo-(6R)-vitamin $D_3$ (2b) using the procedure of Paaren, H. E. et al., *Proc. Natl. Acad. Sci. USA*, 75, 2080 (1978), was reacted with methanesulfonyl chloride (mesyl chloride) (1.1–2.0 eq) in pyridine at 0° C., producing 1-alpha-methanesulfonyloxy-25-hydroxycyclovitamin $D_3$ (3b) in quantitative yield. Treatment of (3b) with a 20-fold excess of potassium thioacetate in dry DMSO at 20° C. exhibited both regio- and stereoselectivity, producing 1-beta-thioacetoxy-25-hydroxy-(6R)-methoxycyclovitamin $D_3$ (4b) (26% yield from 2b).

The $^1$NMR spectrum of (4b) contained peaks at $\delta$0.86(1H, m, H-4); $\delta$2.29(3H, s, SAc); $\delta$3.26(3H, s, OMe); $\delta$4.07(1H, d, $J_{6,7}$=9.1 Hz, H-6), $\delta$4.59(1H, d, J=9.0 Hz, H-1, $\delta$4.97(1H, d, $J_{7,6}$=9.1 Hz, H-7), $\delta$5.20(1H, bs, H-19Z), $\delta$5.29(1H, bs, H-19E).

Intermediate (4b) was typically non-UV absorbing at 254 nm. The IR spectrum of (4b) showed strong stretching absorptions at 1680 cm$^{-1}$(thioacetoxy C=O), and 1080 cm$^{-1}$(ether C—O).

The NMR spectra (250 MHz $^1$H-NMR) were recorded from CDCl$_3$ solutions of the compound containing 0.1% TMS internal standard. All chemical shifts of ($\delta$) are relative to that of TMS which is arbitrarily assigned the value of zero.

Cyloreversion of (4b) in acetic acid at 60° C. afforded 1-beta-thioacetoxy-3-acetoxy-25-hydroxy-vitamin $D_3$ (8b) (22% yield) after separation from its transisomer by TLC on silica gel followed by reverse phase HPLC. Stereochemical assignments at H-1 were based on comparison of the $^1$H-NMR spectra of 1-alpha-3-beta-diacetoxyvitamin D analogues of known stereochemistry, and on mechanistic considerations as disclosed by Paaren, H. E. et al., *Arch. Biochem. Biophys.*, 209, 579 (1981).

$^1$H-NMR spectrum of (8b): $\delta$0.53(3H, s, H$_3$-18); $\delta$0.94(3H, d, $J_{20,21}$=6.4 Hz), H$_3$-21); $\delta$ 1.23(6H, s, H$_3$-26, 27); $\delta$ 2.08(3H, s, OAc); $\delta$ 2.33(3H, s, SAc); $\delta$ 4.42(1H, m, H-1); $\delta$ 4.94(1H, bs, H-19Z); $\delta$5.04(1H, m, H-3); $\delta$5.38(1H, bs, H-19E); $\delta$5.92 and 6.34(1H, ABq, $J_{6,7}$=11 Hz, H-7 and H-6).

UV spectra of (8b) exhibited a broad $\lambda_{max}$ at 265 nm and a $\lambda_{min}$ at 228 nm characteristic of vitamin D.

The IR spectrum of (8b) contained strong stretch absorptions at 1725 cm$^{-1}$(acetoxy C=O), 1685 cm$^{-1}$ (thioacetoxy C=O), and 1250 cm$^{-1}$(acetoxy C—O).

Careful hydrolysis (4% KOH in methanol) of (8b) under argon, followed by acidification with acetic acid and purification by reverse phase HPLC, furnished the final product (1b).

A broad $\lambda_{max}$ at 265 nm and $\lambda_{min}$ at 228 nm in the UV spectrum of (1b) was characteristic of vitamin D.

Mass spectrometry (E.I.) of (8b) gave a molecular ion at m/z 432 and fragment ions corresponding to loss of water, H$_2$S, sidechain, and 7,8-bond cleavage.

EXAMPLE 7

To a solution of 1-alpha-hydroxy-(6R)-methoxycyclovitamin $D_3$ (115.7 mg) and triphenylphosphine (84.2 mg) in absolute benzene (1.5 ml) was added a solution of p-nitrobenzoic acid (53.6 mg) in dry THF (0.7 ml), and the solution stirred at room temperature. After 10 minutes, a solution of diethylazodicarboxylate ester (55.8 mg, 50.5 ul) in absolute benzene (0.2 ml) was added and the reaction mixture stirred overnight, when TLC indicated completion. The solvent was removed under reduced pressure, and the residue was dissolved in ethyl acetate. This was washed with saturated $NaHCO_3$, $H_2O$, and NaCl. Separation by TLC eluting with 10% ethyl acetate in hexane gave 1-beta-(p-nitrobenzoyloxy)-(6R)-methoxycyclovitamin $D_3$ (24.0 mg).

1-beta-(p-nitrobenzoyloxy)-(6R)-methoxycyclovitamin $D_3$ (40 mg) was stirred for 15 minutes at room temperature in ether-methanol (1:1) containing KOH (5% w/w), and the reaction mixture diluted with water and extracted with ether. The organic extract was washed with water and dried ($Na_2SO_4$). Purification by TLC eluting 30% ethyl acetate in hexane yielded 1-beta-hydroxy-(6R)-methoxycyclovitamin $D_3$ (25.8 mg).

Having now fully described this invention, it will be apparent to one of ordinary skill in the art that the same way be carried out with minor modifications which do not affect the content or spirit thereof.

What is new and desired to be claimed with Letters Patent is:

1. A biologically active compound having the formula wherein:
(1) R is epoxy or double bond;
(2) $R^1$ is H, an acyl residue or a straight or branched chain glycosidic residue containing 1-20 glycosidic units per residue, or $R^1$ is an orthoester glycoside moiety of the formula:

(II)

in which said formula
(a) A represents a glucofuranosyl or glucopyranosyl ring,
(b) $R^2$ is hydrogen, lower alkyl, aralkyl or aryl, and
(c) $R^3$ is hydrogen or a straight or branched chain glycosidic residue containing 1-20 glyosidic units per residue;

(3) the bond between $C_{22}$ and $C_{23}$ is single or double;
(4) Y is hydrogen, fluorine, methyl or ethyl;
(5) Z is hydrogen, fluorine or $OR^1$; where $R^1$ is defined as above;
(6) X is
(a) hydrogen, or
(b) $OR^1$, wherein $R^1$ is defined as above;
(7) $Q^a$ is $CH_3$, $CF_3$, or $CH_2OR^1$, where $R^1$ is defined as above;
(8) $Q^b$ is $CF_3$ or $CH_3$; and
(9) the $-SR^1$ moiety is in the alpha or beta configuration;
with the proviso that when Y is fluorine, Z is not OH.

2. A biologically active compound having the formula wherein:
(1) $R^1$ is H;
(2) R is a double bond;
(3) the bond between $C_{22}$ and $C_{23}$ is single or double;
(4) Y is hydrogen, fluorine, methyl or ethyl;
(5) Z is hydrogen or fluorine;
(6) X is hydrogen or OH;
(7) $Q^a$ is $CH_3$ or $CF_3$;
(8) $Q^b$ is $CH^3$ or $CF^3$; and
(9) the $-SR^1$ moiety is in the alpha or beta configuration.

3. A biologically active compound having the formula wherein:
(1) R is a double bond;
(2) $R^1$ is H, an acyl residue, or a straight or branched chain glycosidic residue containing 1-20 glycoside units per residue;

(3) the bond between $C_{22}$ and $C_{23}$ is a single or double bond;
(4) Y is hydrogen, fluorine, methyl or ethyl;
(5) Z is hydrogen, fluorine or $OR^1$, where
(6) X is hydrogen or $OR^1$;
(7) $Q^a$ is $CH_3$, $CF_3$, or $CH_2OR$;
(8) $Q^b$ is $CH_3$ or $CF_3$; and
(9) the $-SR^1$ moiety is in the alpha or beta configuration;
with the proviso that when Y is fluorine, Z is not OH.

4. A biologically active compound having the formula wherein:
(1) R is a double bond or epoxy;
(2) $R^1$ is H or an orthoester glycoside moiety of the formula in which said formula
(a) A represents a glucofuranosyl or glucopyranosyl ring, and
(b) $R^2$ is hydrogen, lower alkyl, aryl, or aralkyl, and
(c) $R^3$ is H or a straight or branch chain glycosidic residue containing 1-20 glycosidic units per residue;
(3) the bond between $C_{22}$ and $C_{23}$ is single or double;
(4) Y is hydrogen, fluorine, methyl or ethyl;
(5) Z is hydrogen, fluorine or $OR^1$;
(6) X is hydrogen or $OR^1$;
(7) $Q^a$ is $CH_3$, $CF_3$ or $CH_2OR^1$;
(8) $Q^b$ is $CH_3$ or $CF_3$; and
(9) the $-SR^1$ moiety is in the alpha or beta configuration,
with the proviso that when Y is fluorine, Z is not OH.

5. A compound according to any one of claims 1, 2, 3, or 4 where the $-SR^1$ moiety is in the alpha configuration.

6. A compound according to any one of claims 1, 2, 3, or 4 where the $-SR^1$ moiety is in the beta configuration.

7. A compound according to any one of claims 1, 2, 3, 4, 5 or 6, wherein $R^1$ is hydrogen and X is OH.

8. A compound according to any of claims 1, 2, 3, 4, 5, or 6, wherein X and $R^1$ are hydrogen.

9. A compound according to claim 1 which is 1-alpha-thiovitamin $D_3$.

10. A compound according to claim 1 wherein said compound is 1-alpha-thio-25-hydroxyvitamin $D_3$.

11. A compound according to claim 1 which is 1-beta-thiovitamin $D_3$.

12. A compound according to claim 1 which is 1-beta-thio-25-hydroxyvitamin $D_3$.

13. A pharmaceutical compound comprising the composition of claim 1 and a pharmaceutically acceptable carrier.

14. A method of controlling calcium and phosphorous homeostasis in a mammal comprising administering an effective amount of the compound of claim 1 to said mammal.

15. A method for producing 1-thio derivatives of vitamin D comprising:
(1) reacting 1-hydroxy-(6R)-methoxycyclovitamin D with thioacetic acid in the presence of triphenylphospine and diethylazodicarboxylate to form a first reaction product which is 1-thioacetoxy-(6R)-methoxycyclovitamin D;
(2) reacting said first reaction product with acetic acid to yield a second reaction product which is 1-thioacetoxy-3-beta-acetoxy-vitamin D, said second reaction product demonstrating an inverted stereo configuration to said first reaction product;
(3) hydrolyzing said second reaction product under an inert atmosphere to form a reaction mixture comprising 1-thio vitamin $D_3$; and
(4) acidifying said reaction mixture with acetic acid.

16. A method for producing a compound having the formula (1):

where M is (2):

$R^5$ is H, $CH_3$, or $C_2H_5$, the bond between $C_{22}$ and $C_{23}$ is single or double, and $R^4$ is H or OH comprising;
(A) reacting a compound having the formula (3):

with CH₃SO₂Cl to produce a compound having the formula (4):

(B) reacting (4) with potassium thioacetate to produce the corresponding 1-beta-thioacetoxy-(6R)-methoxy-cyclovitamin D compound having the formula (5):

(C) cycloreverting (5) by reaction with acetic acid to produce the corresponding 1-beta-thioacetoxy-vitamin D compound having the formula (6):

and (D) hydrolysis of (6) to yield the corresponding 1-beta-thiovitamin D compound having the formula (1).

17. The method of claim 16 wherein M is

* * * * *